United States Patent [19]
Liou et al.

[11] Patent Number: 5,839,440
[45] Date of Patent: Nov. 24, 1998

[54] THREE-DIMENSIONAL IMAGE REGISTRATION METHOD FOR SPIRAL CT ANGIOGRAPHY

[75] Inventors: Shih-Ping Liou, West Windsor; Minerva M. Yeung; Boon-Lock Yeo, both of Princeton, all of N.J.

[73] Assignee: Siemens Corporate Research, Inc., Princeton, N.J.

[21] Appl. No.: 261,643

[22] Filed: Jun. 17, 1994

[51] Int. Cl.[6] ....................................................... A61B 6/00
[52] U.S. Cl. ....................... 128/654; 378/98.12; 378/901; 395/119; 395/924
[58] Field of Search ............................. 128/653.1, 653.2, 128/654, 653.4; 364/413.13, 413.14, 413.23, 98.12; 378/4, 901; 395/119, 924

[56] References Cited

PUBLICATIONS

"Smoothing and Matching of 3–D Space Curves", Gueziec et al., Proceedings of the Second European Conference on Computer Vision, May 1992, pp. 620–629.

"CT Angiography with Spiral CT and Maximum Intensity Projection", Napel et al., Radiology, vol. 185, No. 2, Nov. 1992, pp. 607–610.

"Technique for automatic motion correction in digital subtraction angiography", Fitzpatrick et al., Optical Engineering, Nov. 1987, vol. 26, No. 11, pp. 1085–1093.

"Volumetric Rendering of Computed Tomography Data: Principles and Techniques", Ney et al., IEEE Computer Graphics and Applications, Mar. 1990, pp. 24–32.

"An introduction to randomized algorithms", Richard M. Karp, Discrete Applied Mathematics 34 (1991), pp. 165–201.

"Automatic Registration of 3D Images Using Surface Curvature", Thirion et al., SPIE vol. 1768, Mathematical Methods in Medical Imaging (1992), pp. 206–216.

"Volume Rendering", Drebin et al., Computer Graphics, vol. 22, No. 4, Aug. 1988, pp. 65–74.

"Rover Visual Obstacle Avoidance", Hans P. Moravec, Proceedings of the Seventh International Joint Conference on Artificial Intelligence, vol. II, 24–28 Aug. 1981, University of British Columbia, Vancouver, B.C., Canada, pp. 785–790.

"Multi–Modality Image Registration Using Centroid Mapping", Bartoo et al., IEEE Engineering in Medicine & Biology Society 11th Annual International Conference.

"Three–Dimensional Registration of Multimodality Medical Images Using the Principle Axes Tecnique", Moshfeghi et al., Philips J. Res. 47 (1992), pp. 81–97.

"Accurate Three–Dimensional Registration of CT, PET, and/or MR Images of the Brain", Pelizzari et al., Journal of Computer Assisted Tomography, vol. 13, No. 1, 1989, pp. 20–26.

"Closed–form solution of absolute orientation using unit quaternions", Berthold K. Horn, 1987 Optical Society of America, vol. 4, No. 4, Apr. 1987, pp. 629–642.

"A Computational Framework and an Algorithm for the Measurement of Visual Motion", P. Anandan, International Journal of Computer Vision, 2, 1989, pp. 283–310.

"Spiral CT Angiography", Dillon et al. AJR, vol. 160, Jun. 1993, pp. 1273–1278.

"Diagnosis of Cartoid Artery Disease: Preliminary Experience with Maximum–Intensity–Projection Spiral CT Angiography", Marks et al., AJR, vol. 160, Jun. 1993, pp. 1267–1271.

"Common Cartoid Artery Bifurcation: Evaluation with Spiral CT", Schwartz et al., Radiology, vol. 185, No. 2, pp. 513–519.

(List continued on next page.)

*Primary Examiner*—Ruth S. Smith
*Attorney, Agent, or Firm*—Adel A. Ahmed

[57] ABSTRACT

A three-dimensional image registration method also uses an algorithm and applies it to the solution of such problems in 3D CT DSA. The method can deal with incomplete or partial volumetric data in registration and correct patient global motion prior to subtraction even when it is coupled with local unconscious/nonrigid movements. Experimental results demonstrate the effectiveness of this algorithm on several clinical spiral CT data.

24 Claims, 9 Drawing Sheets

OTHER PUBLICATIONS

"Structure Transfer Between Sets of Three Dimensional Medical Imaging Data", Chen et al., Computer Graphics, National Computer Graphics Association, 1985, pp. 171–177.

"The Principal Axes Transformation—A Method for Image Registration", Alpert et al., The Journal of Nuclear Medicine, vol. 31, No. 1, Oct. 1990, pp. 1717–1722.

"Head Fixation Device for Reproducible Position Alignment in Transmission CT and Positron Emission Tomography", Bergstrom et al., Journal of Computer Assisted Tomography, vol. 5, No. 1, 1981, pp. 136–141.

THREE-DIMENSIONAL IMAGE REGISTRATION METHOD FOR SPIRAL CT ANGIOGRAPHY

The present invention relates to spiral computed tomography angiography (CTA) and more specifically to CTA image processing to the suppression of bone image components and the concomitant retention of vessel image components.

Spiral computed tomography angiography (CTA) is a new, minimally invasive technique for vascular imaging, which permits acquisition of a large volume of data in seconds. See E. H. Dillon, M. S. van Leeuwen, et al "Spiral CT angiography," AJR, vol. 160, pp. 1273–1278, June 1993. Much of the research in CTA reported in the professional literature uses three-dimensional (3D) editing/segmentation techniques in one way or another. An objective is to suppress as much bone image related data in the CT image data as possible and still include image data relating to vessels of interest. However, editing introduces a potential for loss or distortion of information and often requires an average 15–30 minutes of operator time. The quality of editing is also very dependent on subjective experience.

Two-dimensional (2D) digital subtraction techniques (commonly known as Digital Subtraction Angiography (DSA)) are conventionally known in the art.

In accordance with an aspect of the present invention, digital subtraction techniques are utilized in three dimensions;

In accordance with another aspect of the present invention a new 3D image registration algorithm is introduced for 3D DSA. Unlike existing techniques which treat a 3D CT image as a series of 2D images sampled at discrete axial positions and which correct motion artifacts of each slice independently, in accordance with the present invention, patient global motion is corrected prior to subtraction even when it is coupled with local unconscious/nonrigid movements. Experimental results have confirmed the effectiveness of the application of the algorithm in accordance with the invention on several sets of clinical spiral CT data.

As has been stated above, spiral CT angiography (CTA) is a new, minimally invasive technique for vascular imaging, which permits acquisition of a large volume of data in seconds.[1] This acquisition speed allows studies to be performed with little patient motion, often in a single breath-hold. If an intravenous (IV) bolus of intravenous contrast material is injected and timed properly, spiral CT scans can capture the arterial phase in a large volume of patient anatomy, thereby providing excellent visualization of vessel lumina, stenoses, and lesions. These data can then be displayed using 3D visualization techniques (e.g., volume-rendering, maximum intensity projection (MIP), and shaded surface display) to give an image of arterial anatomy similar to that of conventional angiography.

Most research in CTA reported in the literature uses editing techniques in one way or the other. See, for example, M. P. Marks, S. Napel, et al. "Diagnosis of carotid artery disease: Preliminary experience with maximum-intensity-projection spiral CT angiography," AJR, vol. 160, pp. 1267–1271, June 1993. S. Napel, M. P. Marks, et al. CT "angiography with spiral CT and maximum intensity projection," Radiology, vol. 185, pp. 607–610, November 1992. R. B. Schwartz, K. M. Jones, et al. "Common carotid artery bifurcation: Evaluation with spiral ct," Radiology, vol. 185, no. 2, pp. 513–519,1992.

As has been stated, the objective is to suppress as much bone image data in the CT data as possible and still include image data on the vessels of interest. The elimination of image data relating to bones and calcific deposits allows MIP reconstruction to display the contrast medium column within the vessel lumen more clearly. However, this editing approach has several limitations. First, editing introduces the potential for loss or distortion of information. This happens when a connectivity algorithm uses too low a threshold to exclude bones that are physically touched by the vessels. It could also occur when the editing procedure attempts to suppress a vessel wall calcification that contacts the vessel lumen. Second, editing typically requires an average 15–30 minutes of operator time and, in some cases, may even take hours. Finally, the quality of editing in most cases is very subjective and variable depending on individual experience. For example, to successfully separate intramural calcium from intraluminal contrast material requires the reference to the unenhanced images.

An alternative approach to spiral CTA is to extend conventional digital subtraction techniques (commonly known as Digital Subtraction Angiography (DSA)) from two dimensions to three dimensions. DSA uses two sets of images: the first set of data are the mask images obtained before opacification, whereas the second set of data, called contrast images are acquired after the injection of a contrast media bolus. The mask related image is subtracted from the contrast related image. If the position of the vessels in the mask and the contrast coincide, the subtraction produces a pure vascular tree image. This ideal situation, however, is hardly ever encountered in clinical practice. In fact, many studies have demonstrated that patient motion is a strong limitation to this subtraction technique and various methods have been suggested to remove the resulting artifact. During data acquisition, head-holding devices can be used to restrict patient motion, while temporal filtering and more commonly, image registration are applied to correct patient motion during post processing. See, for example, L. Eriksson, T. Greitz, T. Ribbe, and L. Widen, "Head fixation device for reproducible position alignment in transmission CT and PET," J. Comp. Assis. Tomgr., pp. 136–141,1981.

Existing DSA techniques treat a 3D CT image as 2D images sampled at discrete axial positions and motion artifacts are corrected independently through registration between each slice of the mask and the contrast image. See for example, J. M. Fitzpatrick, D. R. Pickens et al., "Technique for automatic motion correction in digital substraction angiography" Optical Engineering, vol. 26, pp. 1085–1093, November 1987. However, it is herein recognized that patient motion is three-dimensional in nature and that it should be corrected by finding the three-dimensional motion parameters.

Most prior art 3D image registration techniques are utilized in the fusion of 3D images obtained from various modalities such as CT, PET (Positron Emission Tomography), SPECT (Single Positron Emission Tomography), MRI (Magnetic Resonance Imaging) and ultrasound imaging techniques. Insofar as is known, none of these techniques have been applied to the problem of 3D CTA.

Traditionally, external markers, stereotactic frames and anatomical landmarks are used in applications requiring image registration. See, for example, G. Chen, M. Kessler, and S. Pitluck, "Structure transfer in the 3D medical imaging studies," in Computer graphics, (TX), pp. 171–175, National Computer Graphics Association, 1985.

These methods have to be carried out in controlled environments and require expertise in human anatomical feature identification. A semi-automatic spatial registration scheme for brain images has been developed by Bartoo and Hanson, in which the centroids of anatomical objects are used as fiducial points. See G. Bartoo and W. Hanson "Multi-modality image registration using centroid mapping," IEEE Engineering in Medicine and Biology Society 11th Annual International Conference, 1989. Their technique assumes that the centroid of major anatomical objects remains approximately the same in the presence of distortions and yields results comparable to that of manual registration.

Pelizzari et al. have developed a surface matching technique for 3D registration of multiple brain images. They use the external surface of the head as the reference surface since it is visible in all scans of the brain. See C. Pelizzari, G. Chen, D. Spelbring, R. Weichselbaum, and C. Chen, "Accurate three-dimentional registration of CT, PET, and/or MR images of the brain," Journal of Computer Assisted Tomography, vol. 13, pp. ~20 26, January/February 1989. This reference surface defines a patient-specific coordinate system. The 3D registration is done by finding iteratively the best match between various outlining contours on the serial slices of each scan in the least-squares sense. The motion parameters, namely the rotation, translation and scaling factors, are then computed. Their method can tolerate a certain degree of missing partial surfaces that lie above the head model by excluding them from the least-squares fitting procedure, but the iterative nature requires a good initial estimate for rapid convergence. Human intervention, called "steering", is required to adjust the transformation parameters to ensure a reasonable convergence rate. See C. Pelizzari, G. Chen, D. Spelbring, R. Weichselbaum, and C. Chen, "Accurate three-dimentional registration of CT, PET, and/or MR images of the brain, "Journal of Computer Assisted Tomography, vol. 13, pp. ~20 26, January/February 1989.

Alpert et al use a principal axes transformation technique to register two sets of 3D image data, each of which covers the whole brain volume. See N. Alpert, J. Bradshaw, D. Kennedy, and J. Correia, "The principal axes transformation—a method for image registration," J Nucl Med, vol. 31, pp. 1717–1722, October 1990. The approach computes the center of mass and its principal axes for each data set. The center of mass and three principal axes together define a reference frame. Registration is then obtained by finding how one reference frame can be transformed into the other. Their approach requires manual outline of the volume of interest on which calculations of the center of mass and principal axes are based. This approach offers computational simplicity and speed but suffers from severe limitations, as the whole head must be present in both volumes. See N. Alpert, et al., cited above.

A similar 3D registration method has also been presented by Moshfeghi and Rusinek. They apply an eigenvalue analysis to a sparse matrix for location of the principal axes and then compute the rotation, translation and scaling parameters. They assume no local distortions in images. See M. Moshfeghi and H. Rusinek, "Three-dimensional registration of multimodality medical images using the principal axes technique, "Philips Journal Research, vol. 47, pp. 81–97,1992.

Recently, Thirion et al. have presented an automatic 3D registration algorithm based on the matching of crest lines extracted from both sets of 3D images. Crest lines are the lines corresponding to high curvature points on the surface of the 3D object. Their method first segments the 3D image to extract the object surfaces of interest and then uses the marching line algorithm to automatically extract the crest lines. Crest lines from two data sets are matched based on geometric hashing. See A. Gueziec and N. Ayache, "Smoothing and matching of 3D space curves," in Proceedings of the Second European Conference on Computer Vision, May 1992. At the end of this process, the transform that matches the greatest number of points is retained. See S. B. J.-P. Thirion, O. Monga and etc., "Automatic registration of 3D images using surface curvature," in SPIE Mathematical Methods in Medical Imaging, vol. 1768, pp. 206–216,1992.

The present invention discloses a three-dimensional image registration method using an algorithm applied to the solution of such problems in 3D CT DSA. The invention can deal with incomplete or partial volumetric data in registration and correct patient global motion prior to subtraction even when it is coupled with local unconscious/nonrigid movements. Experimental results have demonstrated the effectiveness of this algorithm on several clinical spiral CT data.

In accordance with an aspect of the invention, a computer-implemented method for three-dimensional image registration in an imaging technique utilizing mask images, and respective data related thereto, obtained before opacification and contrast images acquired after the injection of a contrast media bolus, the method comprises the steps of: resampling serial axial CT mask and contrast images into respective isotropic 3D volumes; selecting 3D feature points in the mask volume; establishing correspondences in the contrast volume; processing resulting sparse 3D image flow vectors by an iterative random algorithm and computing the best motion parameters, translation and rotation, in a least-squares sense that are agreed upon by at least a preset percentage of pairs whereby patient motion is found; after patient motion is found, transforming the mask volume accordingly and subtracting it from the contrast volume; and rendering and displaying a resulting volume.

In accordance with another aspect of the invention, the step of resampling serial axial CT mask and contrast images comprises performing trilinear interpolation for inter-slice voxels; and performing subsampling for voxels in orthogonal directions, namely X and Y directions.

In accordance with another aspect of the invention the step of resampling serial axial CT mask and contrast images reduces image data such that an image registration algorithm can achieve a level of computational efficiency desired in a CTA application.

In accordance with a further aspect of the invention, the image registration algorithm uses only subsampled data associated with points of interest subsampled in the step of performing subsampling to locate 3D feature points of interest.

In accordance with a further aspect of the invention, after the points of interest have been located, the algorithm discards the subsampled data.

In accordance with a further aspect of the invention, after the subsampled data has been discarded, the algorithm refers back to the first mentioned, original image in a subsequent registration process.

In accordance with still a further aspect of the invention, a computer-implemented method for three-dimensional image registration in an imaging technique utilizing mask images, and respective data related thereto, obtained before opacification and contrast images, and respective data related thereto, acquired after the injection of a contrast media bolus, the method comprises the steps of: resampling serial axial CT mask and contrast images into respective isotropic 3D volumes; selecting 3D feature points in the mask volume; establishing correspondences in the contrast volume; processing resulting sparse 3D image flow vectors by an iterative random algorithm as follows: (a) start with a desired maximum individual residual error $\epsilon$ and desired size s, (b) select randomly a small number of points, say $N_1'$, from V to form S and the corresponding points from W to form S', (c) compute the rotation matrix R and the translation vector t for S and S' using unit quaternions and if the maximum individual residual error is greater than $\epsilon$, repeat this step until such is no longer the case, (d) randomly pick a fixed number of new points from the remaining ones in V and W, and compute new transform parameters and, if the error constraint is again satisfied, append these points to S and S' and if not, this step otherwise, (e) repeat step d) until the size of S and S' is greater than or equal to s, at which point terminate with V'← S and W'← S', or restart with step b) if, after a predetermined number of times, T1, of repeating of step d, the size of S does not reach s, or restart with step b) with a new $\epsilon$ (i.e. $\epsilon \leftarrow \epsilon + \Delta\epsilon$) if for the given e, the desired size s is not obtained after a predetermined number of restarts, T2.

In accordance with still another aspect of the invention, after a rotation matrix and a translation vector are computed, a geometric transformation is carried out.

In accordance with still yet another aspect of the invention, the mask volume is transformed according to new transform parameters and resampled to an isotropic volume for display purposes, the contrast volume is also resampled to an isotropic volume of the same dimension, sub-voxel intensity values are computed by trilinear interpolation, subtraction of resampled contrast volume by the geometrically transformed and resampled mask volume yields a subtracted DSA volume, the subtracted DSA volume is rendered using a commercially available application, the Ney/Fishman's volume renderer Iprender, the rendering algorithm outputs a variable number of images each of which corresponds to a projection at a different viewing angle, and rendered results are reviewed using an animator program for providing a fast display of successive frames so as to allow a radiologist to synthesize a greater amount of depth information, which otherwise is not available from static viewing.

In accordance with another aspect of the invention, the method comprising the steps of: selecting a set of 3D feature points in the mask volume; and establishing correspondences with a set of points in the contrast volume.

In accordance with yet a further aspect of the invention, a rotation matrix and a translation vector are obtained for transforming the mask volume to the contrast volume, the rotation matrix and the translation vector are computed subject to a minimization of sums of squares of errors, centroids of the two sets of data points are obtained, a cross-covariance matrix is computed, the cross-covariance matrix having elements which are respective sums of products of coordinates in the two data sets, the unit quaternion is obtained as the unit eigenvector corresponding to a most positive eigenvalue of a symmetric matrix, the symmetric matrix is a 4×4 matrix whereof elements are the respective sums of products of coordinates in the two data sets, and an optimal translation vector is then derived as the difference between (A) the centroid of the set of points in the contrast volume, and (B) the product of the centroid of the set of 3D feature points in the mask volume and the rotation matrix.

The present invention will be better understood from the following detailed description of preferred embodiments, in conjunction with the drawing, in which FIG. 1 shows a flow chart in accordance with the invention;

Figure 1:
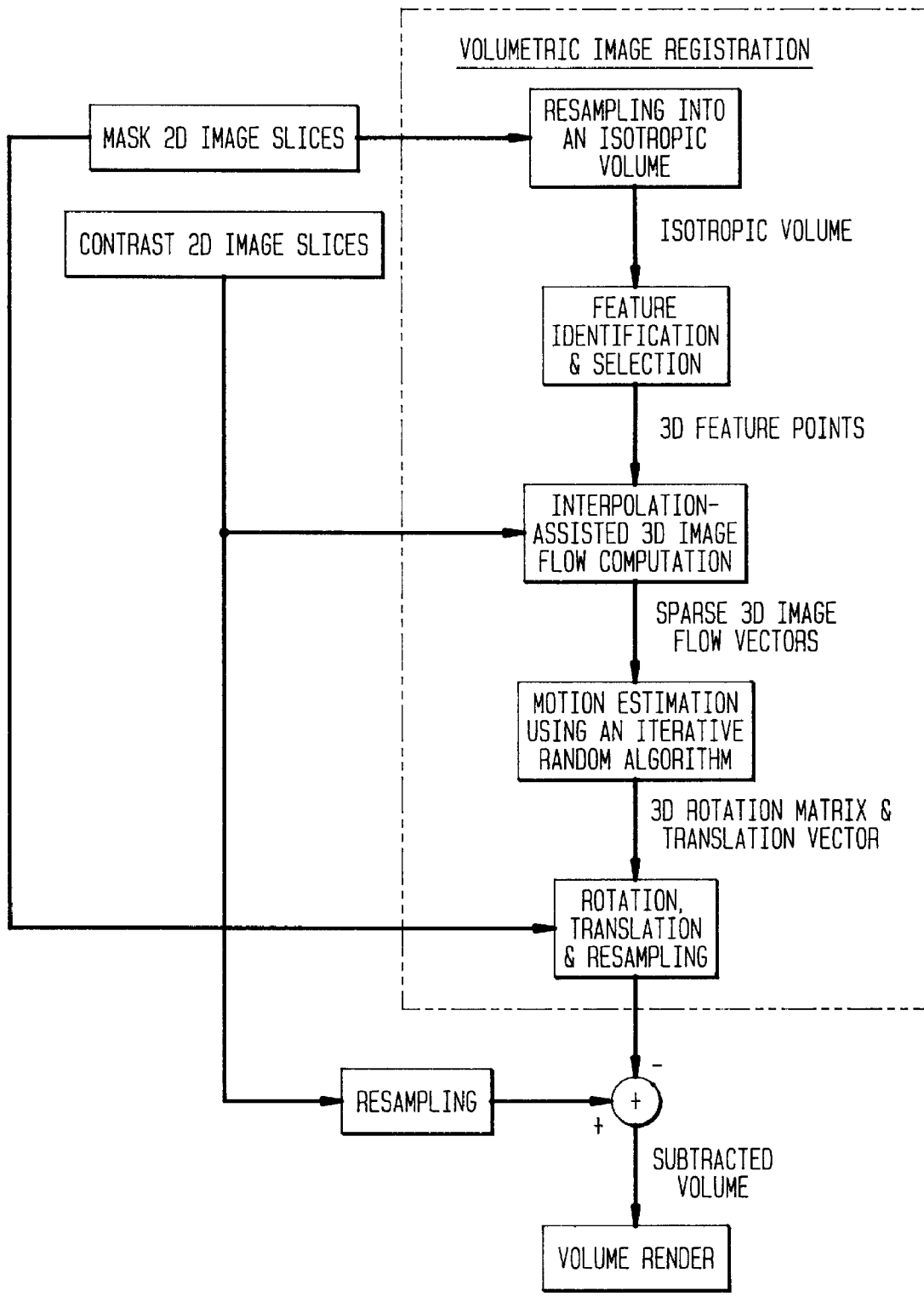

The chart in FIG. 1 illustrates various steps of the present invention. Serial axial CT images are first resampled into an isotropic 3D volume, that is, a volume exhibiting isotropic image resolution. 3D feature points in the mask volume are then selected and correspondences are established in the contrast volume. The resulting sparse 3D image flow vectors are then processed by an iterative random algorithm to compute the best motion parameters (translation and rotation) in the least-squares sense that are agreed upon by at least preset percentage of pairs. After the patient motion is found, the mask volume is transformed accordingly and subtracted from the contrast volume. The resulting subtracted volume is then rendered and viewed on the display. The method will next be explained in greater detail.

The first step in accordance with the invention is to resample the original mask images into an isotropic data set. In this context, a voxel is an elemental three-dimensional image component, for example an elemental cube, by analogy with a pixel in two dimensions, for example, an elemental square. Trilinear interpolation is used for inter-slice voxels, while subsampling is applied to voxels in the X and the Y directions. This resampling process reduces image data and therefore allows the algorithm in accordance with the invention to achieve the level of computational efficiency desired in a CTA application.

However, unlike prior art approaches which use subsampling techniques, the present invention does retain the level of accuracy critical to the success of image registration. The image registration algorithm in accordance with the present invention uses the subsampled points only to locate 3D feature points. After locating these points of interest, the algorithm discards the subsampled data and always refers back to the original image in any subsequent registration process. This aspect will become more clear further in the present description.

Figure 2:
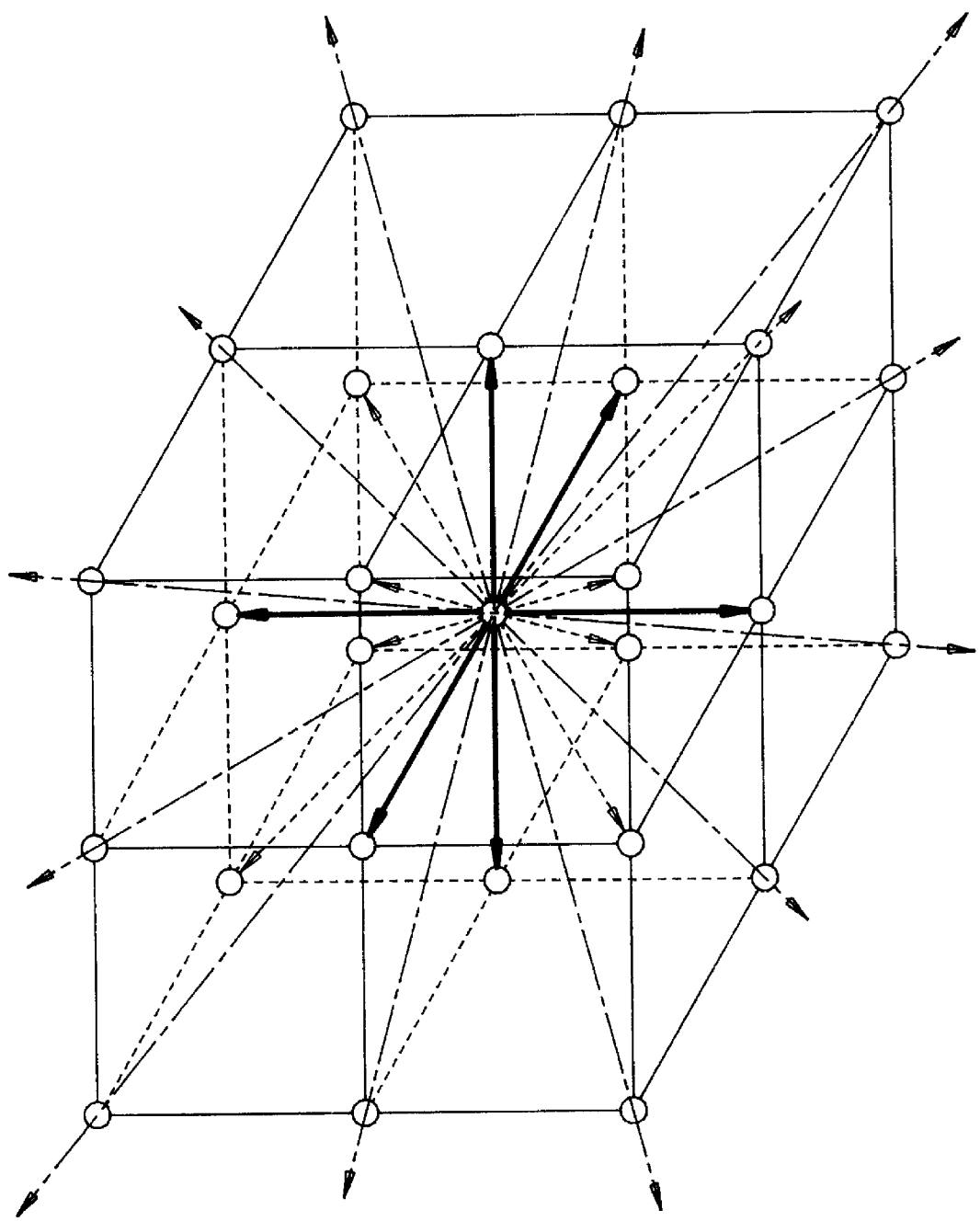
FIG. 2 shows a vector representation helpful to an understanding of the invention and showing the 13 directions for finding the 3D feature points.

Distinct 3D features tend to be likely to have unique matches and thus will improve the accuracy of image registration. Most feature detection work reported in the prior art is for two-dimensional images. Three-dimensional features are difficult to visualize and require a substantial amount of time to locate. The interest operator described by Moravec from 2D to 3D is herein extended and found to be not only fast but also to work very well. See H. P. Moravec, "Rover visual obstacle avoidance," in Proceedings of the 7th International Conference on Artificial Intelligence, (Vancouver, B.C., Canada), pp. 785–790, August 1981. In the two dimensional case, the interest operator computes the sum of the squares of intensity differences (an estimation of the variance) at every pixel position for four possible directions. The interest value is defined as the minimum of all variance values. When the operator is extended to three dimensions, it computes at every voxel position the interest index, defined to be the minimum of the variance values in all the possible 13 directions as shown in FIG. 2.

Figure 3A:
FIG. 3 shows sample images illustrative of the invention.
Figure 3B:
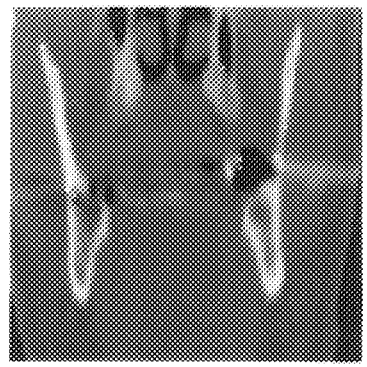
Figure 3C:

Mathematically, this interest index i can be written as follows:

$$i(\vec{v}) = \min_{\vec{\omega}_j \in \Lambda} \sum_{k \in \Omega, a \in \{-1,1\}} (I(\vec{v} - a(k+1)\vec{\omega}_j) - I(\vec{v} - ak\vec{\omega}_j))^2 \quad (1)$$

where $\vec{v}$ = $(x, y, z)$ is current voxel position $I(\vec{v})$ : intensity value at $(x, y, z)$ $\omega$ = $\{n : n \in N, n < \lfloor \text{window size}/2 \rfloor\}$ $\Lambda$ = $\{\vec{\omega}_1 = (0, 0, 1), \vec{\omega}_2 = (0, 1, 0), \vec{\omega}_3 = (0, 1, 1), \vec{\omega}_4 = (1, 0, 0), \vec{\omega}_5 = (1, 0, 1), \vec{\omega}_6 = (1, 1, 0), \vec{\omega}_7 = (1, 1, 1), \vec{\omega}_8 = (0, -1, 1), \vec{\omega}_9 = (-1, 0, 1), \vec{\omega}_{10} = (-1, 1, 0), \vec{\omega}_{11} = (-1, 1, 1), \vec{\omega}_{12} = (-1, -1, 1), \vec{\omega}_{13} = (1, -1, 1)\}$ The algorithm then selects a preset number of points with the highest interest indices to be the feature points. To ensure a more evenly distributed feature points in the entire volume, a local maxima filter is applied to avoid the clustering of feature points in small volumes. FIG. 3 shows some of the feature points selected in three 2D image slices from different views of the head portion, namely: (left) axial view; (middle) coronal view; (right) sagittal view.

Following the selection of feature points is the estimation of the 3D image flow field, with the use of interpolation-assisted 3D image flow computation. For each feature point p at location $\vec{V}_p = (x, y, z)$ in the mask volume $I_m$ a correlation-window $\Omega_p$ of size $(2M+1) \times (2M+1) \times (2M+1)$ is formed around the voxel. A search window $\Omega_S$, of size $(2N+1) \times (2N+1) \times (2N+1)$ is established around the voxel at location $(x, y, z)$ in the contrast volume $I_c$. The error distribution e is computed for every possible position $\vec{\delta v}$ in the search window using sum-of-squared-differences as:

$$e(\vec{\delta v}) = \sum_{\omega \in \Omega} (I_m(\omega) - I_c(\omega + \vec{\delta v}))^2 \quad (2)$$

where $\Omega = \{\vec{\omega} : \|\vec{\omega} - \vec{v}\| \leq M\}$

The $\vec{\delta v}$ ($\vec{v}_c = \vec{v}_m + \vec{\delta v}$) that gives the minimum error distribution is selected as the 3D image flow vector. It is herein recognized that this exhibits a type of correspondence to a hypothetical extension of Anandan's work on optical flow computation to three dimensions, such extension has not been recognized in the prior art insofar as is known. See P. Anandan, "A computational framework and an algorithm for the measurement of visual motion," International Journal of Computer Vision, vol. 2, pp. 283–310, 1989.

Thus, there are several major differences between the present invention and a hypothetical 3D extension of Anandan's technique, as herein recognized. First, in the present invention, only the image flow vectors for all selected-feature points are computed, as opposed to the entire 3D volume in the hypothetical 3D extension, which saves a tremendous amount of computation time. Second, $\vec{\delta v}$ can take non-integer values, which means that sub-pixel accuracy in motion estimation can be achieved. Third, even though trilinear interpolation is used when $\vec{\delta v}$ takes a non-integer value, such trilinear interpolation is done only upon demand. In other words, the algorithm does interpolation only on locations within the search window of each selected feature point. Finally, the interpolation always refers back to the values obtained at the original resolution despite of the loss of voxels due to subsampling in the resampling stage. This ensures that subsampling will only improve the computational efficiency and it will not sacrifice the accuracy.

After the image flow field is computed, the algorithm then tries to estimate the patient motion parameters, namely, the translation and the rotation parameters. Motion estimation is thus performed using an iterative random algorithm. In clinical practice, it is hardly possible for patients to remain steady since the entire process takes in the order of 1.5 to 2 minutes. There are certainly local unconscious movements due to muscle contraction, such as the movement of the esophagus.

In accordance with the present invention, an iterative random algorithm is utilized which computes the best motion parameters in the least-squares sense that are agreed upon by at least a predetermined percentage of image flow vectors. This parameter estimation algorithm is based on a quaternion approach and a random algorithm strategy as described in R. M. Karp, "An introduction to randomized algorithms," Discrete Applied Mathematics, vol. 34, pp. 165–210, 1991. See B. K. P. Horn, "Closed-form solution of absolute orientation using unit quaternions," Opt. Soc. Am., vol. 4, pp. 629–642, April 1987. For convenience, a review of the quaternion approach is given in an Appendix for ready reference.

It is well-known that the presence of outliers would severely affect the accuracy of any least squares solution. To obtain an accurate solution, outliers must be detected and removed from the data set. More precisely, it is required to find $$V' = \{\vec{v'}_i\}_{i=1}^{N'} \text{ and } W' = \{\vec{w'}_i\}_{i=1}^{N'}$$

such that $$\max_{i=1 \ldots N'} \|\vec{w'}_i - (R\vec{v'}_i + \vec{t})\|^2$$

can be minimized, subject to $$N' \geq s\% \, N$$

Where v' is the coordinate of the $i^{th}$ point in V', w' is the coordinate of the $i^{th}$ point in W'; and N is the original number of points.

In other words, the biggest possible set of points such that the maximum of residual errors of all points in the set is minimized.

This problem can be solved deterministically through an exhaustive search. However, the execution time and storage requirement will be extremely high. We propose an iterative random algorithm that estimates the optimal solution. This algorithm starts off with a small residual error parameter $\epsilon$, and then seeks to find V' and W' with the maximum individual residual error smaller than $\epsilon$. The solution, for sufficiently small $\epsilon$ will thus approximate the optimal solution. The algorithm is as follows:

1. Start with a desired maximum individual residual error $\epsilon$ and desired size s.
2. Select randomly a small number of points, say $N_1$, from V to form S and the corresponding points from W to form S'. Compute the R and $\vec{t}$ for S and S' using unit quaternions. If the maximum individual residual error is greater than $\epsilon$, repeat this step.
3. Randomly pick a fixed number of new points from the remaining ones in V and W, and compute the new transform parameters. If the error constraint is again satisfied, append these points to S and S'. Repeat this step otherwise.

4. (a) Repeat step 3 until the size of S and S' is greater than or equal to s, at which point terminate with V'←S and W'←S', or (b) restart with step 2 if, after some number of times, T1, of repeating of step 3, the size of S does not reach s, or (c) restart with step 2 with a new $\epsilon$ (i.e. $\epsilon \leftarrow \epsilon + \Delta\epsilon$) if for the given $\epsilon$, the desired size s is not obtained after a large number of restarts, $T_2$.

After the rotation matrix and translation vector are computed, a geometric transformation is carried out. The mask volume is transformed according to these parameters and at the same time, resampled to an isotropic volume for display purposes. The contrast volume is also resampled to an isotropic volume of the same dimension. Sub-voxel intensity values are computed by trilinear interpolation. The subtraction of resampled contrast volume by the geometrically transformed (and resampled) mask volume yields the subtracted DSA volume.

The subtracted DSA volume is rendered using a commercially available application, the Ney/Fishman's volume renderer IPRENDER. The volumetric rendering technique was originally developed by Drebin et al. and later applied to CT data. See R. A. Drebin, L. Carpenter, and P. Hanrahan, "Volume rendering," Computer Graphics (Proc. SIGGRAPH), vol. 22, pp. 65–74, August 1988 and D. R. Ney, E. K. Fishman, and D. Magid, "Volumetric rendering of computed tomography data: Principles and techniques," IEEE Computer Graphics and Applications, pp. 24–32, March 1990.

The rendering algorithm outputs a variable number of images each of which corresponds to a projection at a different viewing angle. Rendered results are reviewed using an animator program. The fast display of successive frames allows radiologists to synthesize a greater amount of depth information, which otherwise is not available from static viewing.

$$\sum_{i=1}^{n} \|\vec{w}_i - (R\vec{v}_i + \vec{t})\|^2, \tag{3}$$

A quaternion based algorithm is used to compute the motion parameters. The algorithm is reviewed here. For more details, refer to B. K. P. Horn, "Closed-form solution of absolute orientation using unit quaternions," Opt. Soc. Am., vol. 4, pp. 629–642, April 1987.

The unit quaternion is a four vector $q_R = [q_0 \ q_1 \ q_2 \ q_3]^t$ where $q_0 \geq 0$, and $q_0^2 + q_1^2 + q_2^2 + q_3^2 = 1$. It is an alternative way to represent a unit rotation.

$$R = \begin{pmatrix} q_0^2 + q_1^2 + q_2^2 + q_3^2 & 2(q_1 q_2 - q_0 q_3) & 2(q_1 q_3 + q_0 q_2) \\ 2(q_1 q_2 + q_0 q_3) & q_0^2 + q_2^2 - q_1^2 - q_3^2 & 2(q_2 q_3 - q_0 q_1) \\ 2(q_1 q_3 - q_0 q_2) & 2(q_2 q_3 + q_0 q_1) & q_0^2 + q_3^2 - q_1^2 - q_2^2 \end{pmatrix} \tag{4}$$

The centroids $\vec{\mu}_v$ of the set V and $\vec{\mu}_w$ of the set W are given by $$\vec{\mu}_v = \frac{1}{N} \sum_{i=1}^{N} \vec{v}_i \tag{5}$$

and $$\vec{\mu}_w = \frac{1}{N} \sum_{i=1}^{N} \vec{w}_i \tag{6}$$

To determine of the quaternion $\vec{q}R$, the 3×3 cross-covariance matrix $$M = \sum_{i=1}^{N} (\vec{v}_i - \vec{\mu}_v)(\vec{w}_i - \vec{\mu}_w)^t \tag{7}$$

is first computed. Its elements are the sums of products of coordinates in V and W. This matrix contains all the information required to solve the least-squares problem for rotation. Note that M may be written in the form $$M = \begin{pmatrix} S_{xx} & S_{xy} & S_{xz} \\ S_{yx} & S_{yy} & S_{yz} \\ S_{zx} & S_{zy} & S_{zz} \end{pmatrix} \tag{8}$$

where $$S_{xx} = \sum_{i=1}^{N} x_{v,i} x_{w,i}, \tag{9}$$

$$S_{xy} = \sum_{i=1}^{N} x_{v,i} y_{w,i},$$

and so on, and where $\vec{v}_i = [X_{v,i} Y_{v,i} Z_{v,i}]^t$ and $\vec{W}_i = [X_{w,i} Y_{w,i} Z_{w,i}]^t$.

The unit quaternion of interest is then the unit eigenvector corresponding to the most positive eigenvalue of the 4×4 symmetric matrix N, where $$N = \tag{10}$$

$$\begin{pmatrix} S_{xx} + S_{yy} + S_{zz} & S_{yz} - S_{zy} & S_{zx} - S_{xz} & S_{xy} - S_{yx} \\ S_{yz} - S_{zy} & S_{xx} - S_{yy} - S_{zz} & S_{xy} - S_{yx} & S_{zx} - S_{xz} \\ S_{zx} - S_{xz} & S_{xy} - S_{yx} & -S_{xx} - S_{yy} - S_{zz} & S_{yz} + S_{zy} \\ S_{xy} - S_{yx} & S_{zx} + S_{xz} & S_{yz} + S_{zy} & -S_{xx} - S_{yy} + S_{zz} \end{pmatrix}$$

The optimal translation vector is then given by $$\vec{t} = \vec{\mu}_w - R\vec{\mu}_v.$$

In an experimental implementation in accordance with the present invention, two sets of images of the lower portion of a patient's head (from upper neck portion to the region below the eyes) were acquired using the Siemens Somatom Plus Spiral Volumetric Computed Tomography (CT) scanners. Since this was only a trial run, no special care was taken in the data acquisition process. The time latency between two scans is known to be in the order of several minutes.

The pixel size of each image slice is 0.29697 mm in both the X and the Y direction, with an interslice separation of 3 mm. The resolution for both image sets is 512 pixels×512 pixels and a total of 57 slices per image set. Data acquired have an intensity value range between 0 and 2047. The patient has been scanned from the neck up to near the circle of willis. The lower half of the scans involve the neck where much nonrigid motion is concentrated.

Figure 4:
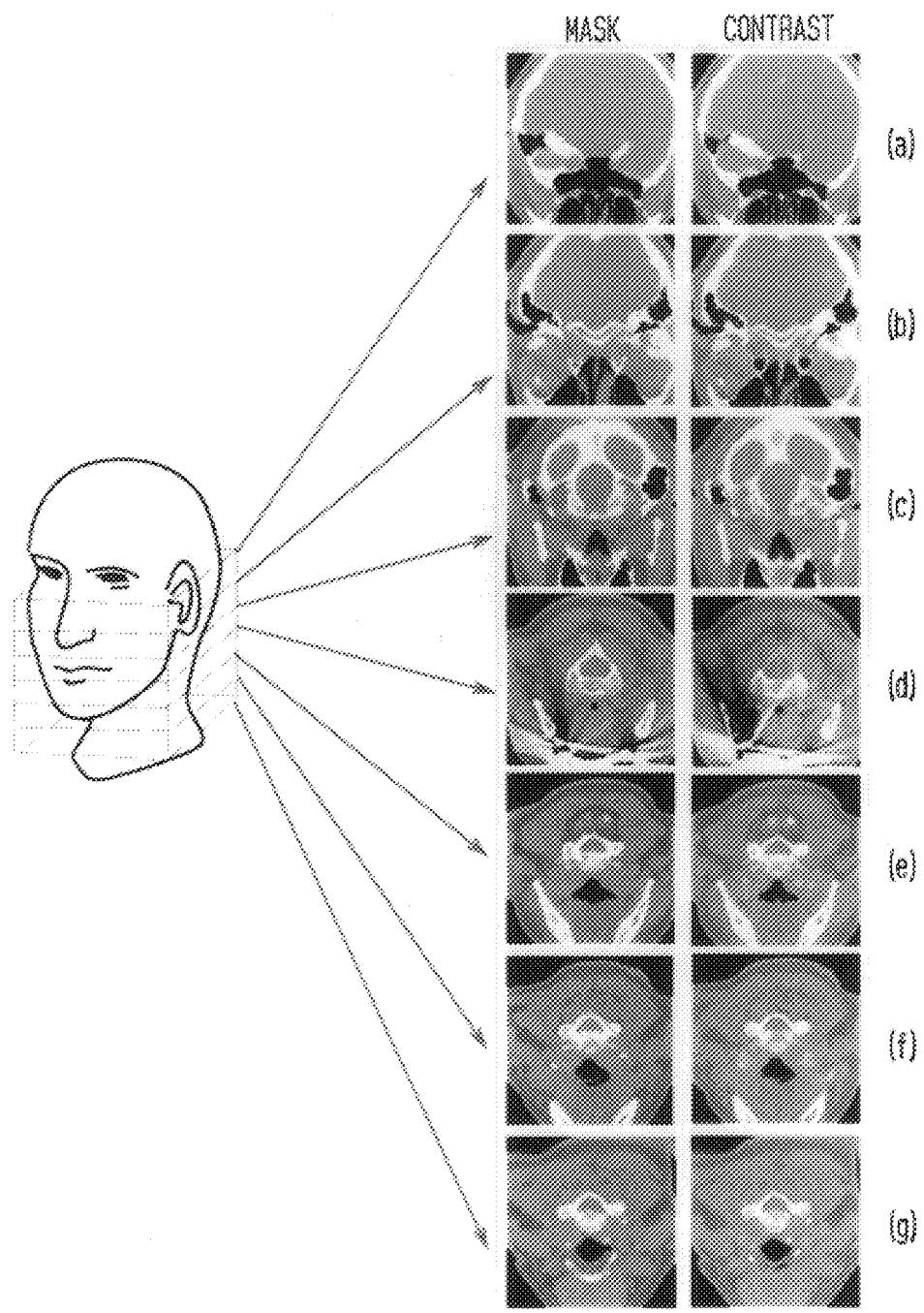
FIG. 4 shows a graphic representation and sample images relating to an aspect of the invention.

The image sets are known to have significant defects in twelve of the 57 slices (slice number 20 to 32) due to two gold teeth inside the mouth. FIG. 4 shows some of the 2D mask and contrast image slices acquired.

The approach in accordance with the present invention took less than 13 minutes of CPU time at the resolution of 128×128×144 on a SUN SPARCstation 10, including the input of the original data, the resampling process, the 3D image registration, the geometric transformation and the final output of the subtracted volume. At the resolution of 256×256×288, it takes longer CPU time, most of which is spent on I/O, geometric transformation and resampling. The feature selection, matching and parameter estimation portion take roughly the same CPU time, as the computational complexity is mainly dependent upon the number of feature points used which, in the present, is 300 in both cases.

Figure 5A:
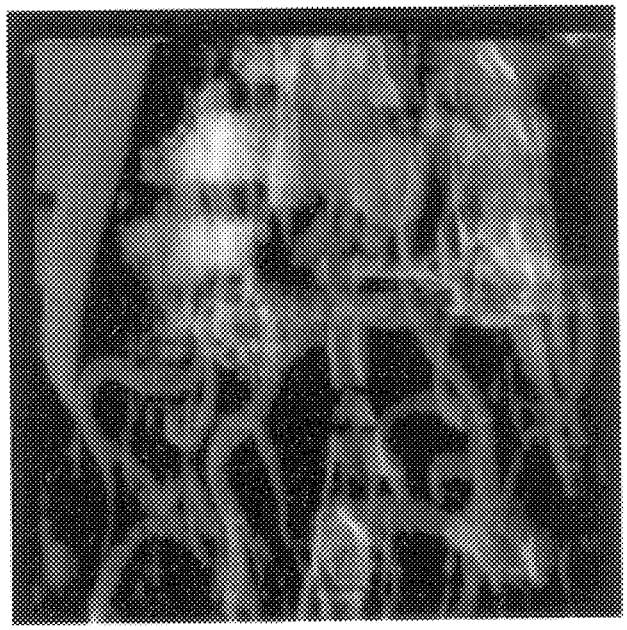
FIG. 5, 6, 7, 8, and 9 show various sample images for illustrating the invention.
Figure 5B:
Figure 6A:
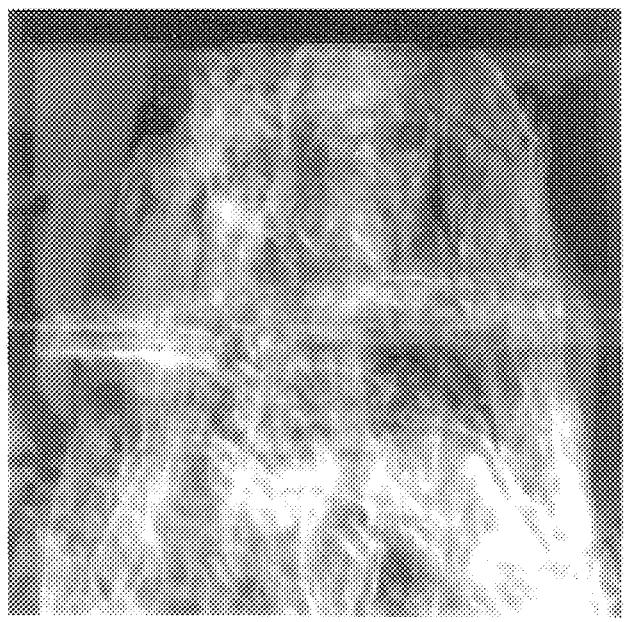
Figure 6B:
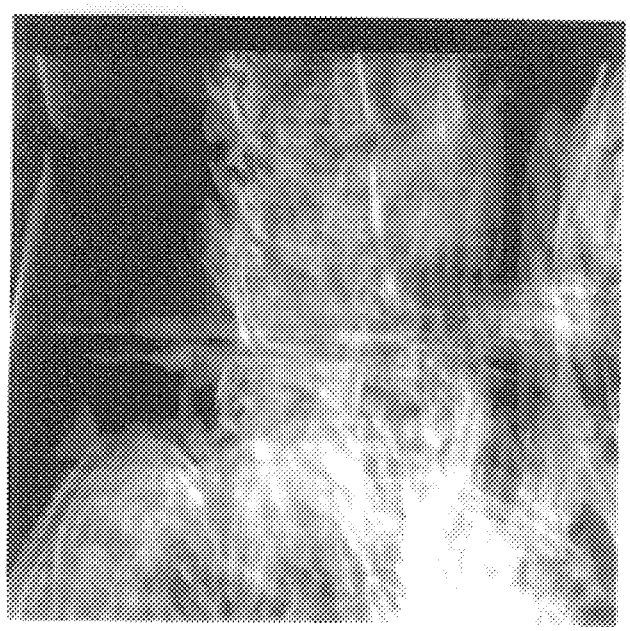
Figure 7A:
Figure 7B:
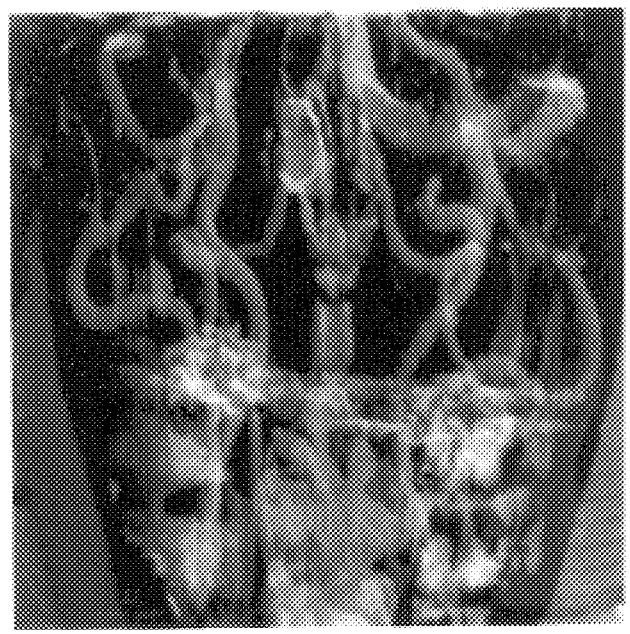
Figure 8A:
Figure 8B:

The rendered subtracted volume is displayed on the screen using an animation software. Snapshots of the animation display are captured on the screen and shown in FIG. 5. Other views of the same volume from different angles are shown in FIG. 7. As a comparison, the subtracted volumes from the same views are shown in FIG. 6 and FIG. 8. They are produced by subtracting directly (without registration) the resampled mask volume from the resampled contrast volume.

Figure 9:
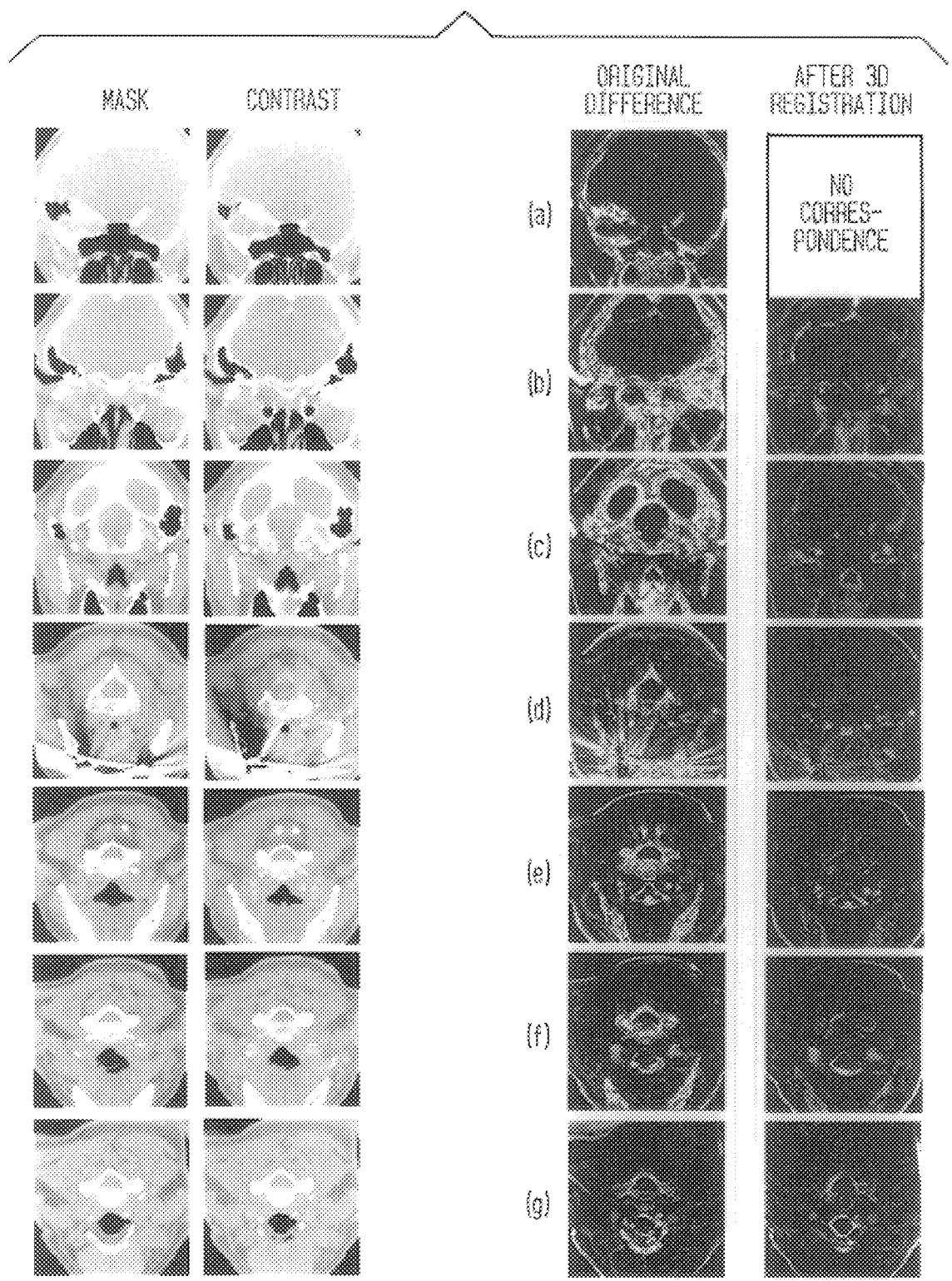

In addition, several two-dimensional axial slices of the subtracted volume are displayed in FIG. 9 to show the improvement due to registration. The darker the intensity value is, the better the position of the vessels in the mask and the contrast coincides.

The CTA volume of the registered image set improved significantly the visualization of cerebral blood vessels in 3D space over the unregistered one. Despite the CTA approach we developed in general offered a high degree of visibility of the blood vessels in most portions of the head region scanned.

The results clearly demonstrate that the majority of patient movements have been corrected. The algorithm is able to avoid the influences of imaging artifacts due to two implanted gold teeth. There are left, however, muscle contraction of the esophagus (by the swallowing action of the patient) and movement of the lower jaw (which might have accompanied the swallowing action).

The algorithm for 3D CTA in accordance with the invention offers at least the following advantages:

A. The algorithm is fast compared to the time required for operator-assisted editing.
B. The registration algorithm can successfully eliminate images of bones and retain the images of vessels of interest even if the former are physically touched by the latter.
C. The algorithm can deal with 3D patient motion as well as imprecision of table movement during the scanning process.
D. The 3D interest operator is fast and works very well in detecting 3D corner points.
E. Although the registration algorithm subsamples the original image to improve its computational efficiency, it always refers back to the original image at every stage of computation, leading to the desired sub-pixel accuracy.
F. While the global patient motion is always coupled with local unconscious/non-rigid motion, the iterative random algorithm is able to correct the majority of patient motion prior to the subtraction process.
G. The algorithm can easily be adapted to other medical applications such as multi-modality data fusion that requires 3D image registration.

The invention is intended to be practiced by computer implementation. While the present invention has been described and explained by way of exemplary embodiments, it should be understood that various changes and modifications apparent to one of skill in the art to which it pertains may be made in the implementation without departing from the spirit of the invention. Such changes are contemplated to be within the scope of the invention which is defined by the claims.

What is claimed is:

1. A computer-implemented method for three-dimensional image registration in an imaging technique utilizing mask images, and respective data thereto, obtained before opacification and contrast images acquired after the injection of a contrast media bolus, said method comprising the steps of:
   resampling serial axial CT mask and contrast images into respective isotropic 3D volumes;
   selecting 3D feature points in said mask volume;
   establishing correspondences in said contrast volume;
   processing resulting sparse 3D image flow vectors by an iterative random algorithm and computing motion parameters, translation and rotation, in a least squares optimized sense that are agreed upon by at least a preset percentage of pairs whereby patient motion is found;
   after patient motion is found, transforming said mask volume accordingly and subtracting it from said contrast volume; and
   rendering and displaying a resulting volume.

2. A computer-implemented method in accordance with claim 1 wherein said step of resampling serial axial CT mask and contract images comprises:
   performing trilinear interpolation for inter-slice voxels; and
   performing subsampling for voxels in orthogonal directions.

3. A computer-implemented method in accordance with claim 1 wherein said step of resampling serial axial CT mask and contrast images reduces image data such that an image registration algorithm can achieve a level of computational efficiency desired in a computed tomography angiography CTA application.

4. A computer-implemented method in accordance with claim 1 wherein said image registration algorithm uses only subsampled data associated with points of interest subsampled in said step of performing subsampling to locate 3D feature points of interest.

5. A computer-implemented method in accordance with claim 4 wherein after said points of interest have been located, said algorithm discards said subsampled data.

6. A computer-implemented method in accordance with claim 5 wherein after said subsampled data has been discarded, said algorithm refers back to said first mentioned, original image in a subsequent registration process.

7. A computer-implemented method for three-dimensional image registration in an imaging technique utilizing mask images, and respective data related thereto, obtained before opacification and contrast images, and respective data related thereto, acquired after the injection of a contrast media bolus, said method comprising the steps of:
   resampling serial axial CT mask and contrast images into respective isotropic 3D volumes;
   selecting 3D feature points in said mask volume;
   establishing correspondences in said contrast volume;
   processing resulting sparse 3D image flow vectors by an iterative random algorithm as follows:
   (a) start with a desired maximum individual residual error $\epsilon$ and desired size s;
   (b) select randomly a small number of points, $N_i$, from a set of points in said mask volume, V to form S and the corresponding points from a set of points in contrast volume, W to form S';

(c) compute a rotation matrix R and a translation vector t for a set S and a set S' using unit quaternions and if the maximum individual residual error is greater than $\epsilon$, repeat this step until such is no longer the case;

(d) randomly pick a fixed number of new points from the remaining ones in V and W, and compute new transform parameters and, if the error constraint is again satisfied, append these points to S and S' and if not, repeat this step; and (e) repeat step (d) until the size of S and S' is greater than or equal to s, at which point terminate with V'←S and W'←S', or restart with step (b) if, after a predetermined number of times, T1, of repeating step (d), the size of S does not reach s, or restart with step (b) with a new $\epsilon$ if for the given $\epsilon$, the desired size s is not obtained after a predetermined number of restarts, T2.

8. A computer-implemented method in accordance with claim 7 wherein after said rotation matrix and a translation vector are computed, a geometric transformation is carried out.

9. A computer-implemented method in accordance with claim 8 wherein said mask volume is transformed according to new transform parameters and resampled to an isotropic volume for display purposes.

10. A computer-implemented method in accordance with claim 9 wherein said contrast volume is also resampled to an isotropic volume of the same dimension.

11. A computer-implemented method in accordance with claim 10 wherein sub-voxel intensity values are computed by trilinear interpolation.

12. A computer-implemented method in accordance with claim 11 including a rendering step wherein subtraction of resampled contrast volume by the geometrically transformed and resampled volume is performed to yield a subtracted DSA volume.

13. A computer-implemented method in accordance with claim 12 wherein said rendering step is performed using a known type of renderer.

14. A computer-implemented method in accordance with claim 13 wherein said rendering step is performed so as to result in a variable number of images each of which corresponds to a projection at a different viewing angle.

15. A computer-implemented method in accordance with claim 14 wherein rendered results are reviewed using an animator program for providing a fast display of successive frames.

16. A computer-implemented method for three-dimensional image registration in an imaging technique utilizing mask images, and respective data related thereto, obtained before opacification and contrast images, and respective data related thereto, acquired after the injection of a contrast media bolus, said method comprising the steps of:

resampling serial axial CT mask and contrast images into respective isotropic 3D volumes;

selecting a set of 3D feature points in said mask volume;

establishing correspondence with a set of points in said contrast volume;

processing resulting sparse 3D image flow vectors by an iterative random algorithm as follows:

(a) start with a desired maximum individual residual error $\epsilon$ and desired size s;

(b) select randomly a small number of points, $N_i$, from a set of points in said mask volume, V to form S and the corresponding points from a set of points in said contrast volume, W to form S';

(c) compute a rotation matrix R and a translation vector t for a set S and a set S' using unit quaternions, wherein a unit quaternion expresses a unit rotation, and if the maximum individual residual error is greater than $\epsilon$, repeat this step until such is no longer the case;

(d) randomly pick a fixed number of new points from the remaining ones in V and W, and compute new transform parameters and, if the error constraint is again satisfied, append these points to S and S' and if not, repeat this step; and (e) repeat step (d) until the size of S and S' is greater than or equal to s, at which point terminate with V'←S and W'←S', or restart with step (b) if, after a predetermined number of times, T1, of repeating step (d), the size of S does not reach s, or restart with step (b) with a new $\epsilon$ if for the given $\epsilon$, the desired size s is not obtained after a predetermined number of restarts, T2.

17. A computer-implemented method in accordance with claim 16 wherein in step (c) a rotation matrix and a translation vector are obtained for transforming said mask volume to said contrast volume.

18. A computer-implemented method in accordance with claim 17 wherein said rotation matrix and said translation vector are computed subject to a minimization of sums of squares of errors.

19. A computer-implemented method in accordance with claim 18 wherein respective centroids of said rotation matrix and said translation vector are obtained.

20. A computer-implemented method in accordance with claim 19 wherein a cross-covariance matrix is computed, said cross-covariance matrix having elements which are respective sums of products of coordinates in said rotation matrix and said translation vector.

21. A computer-implemented method in accordance with claim 20 wherein said unit quaternions are obtained as the unit eigenvector corresponding to a most positive eigenvalue of a symmetric matrix.

22. A computer-implemented method in accordance with claim 21 wherein said symmetric matrix is a 4×4 matrix whereof elements are said respective sums of products of coordinates in said rotation matrix and said translation vector.

23. A computer-implemented method in accordance with claim 22 wherein an optimal translation vector is then derived as the difference between (A) said centroid of said set of points in said contrast volume, and (B) the product of said centroid of said set of 3D feature points in said mask volume and said rotation matrix.

24. A computer-implemented method for three-dimensional image registration in accordance with claim 7, wherein step (c) of computing motion parameters R and t is performed in accordance with the following steps:

compute R and t subject to the minimization of the sums of squares of errors $$\sum_{i=1}^{n} \|\vec{w_i} - (R\vec{v_i} + \vec{t})\|^2,$$

utilizing a quaternion based algorithm, wherein a unit quaternion is a four vector $q_R = [q_0\ q_1\ q_2\ q_3]^t$ where $q_0 \geq 0$, and $q_0^2 + q_1^2 + q_2^2 + q_3^2 = 1$ and is way to represent a unit rotation, R being computed as:

$$R = \begin{pmatrix} q_0^2 + q_1^2 + q_2^2 + q_3^2 & 2(q_1q_2 - q_0q_3) & 2(q_1q_3 + q_0q_2) \\ 2(q_1q_2 + q_0q_3) & q_0^2 + q_2^2 - q_1^2 - q_3^2 & 2(q_2q_3 - q_0q_1) \\ 2(q_1q_3 - q_0q_2) & 2(q_2q_3 + q_0q_1) & q_0^2 + q_3^2 - q_1^2 - q_2^2 \end{pmatrix};$$

compute centroids $\mu_v$ V of the set V and $\mu_w$ of the set W in accordance with $$\vec{\mu}_v = \frac{1}{N} \sum_{i=1}^{N} \vec{v}_i$$

and $$\vec{\mu}_w = \frac{1}{N} \sum_{i=1}^{N} \vec{w}_i$$

compute a 3×3 cross-covariance matrix M, $$M = \sum_{i=1}^{N} (\vec{v}_i - \vec{\mu}_v)(\vec{w}_i - \vec{\mu}_w)^t$$

whereof the elements are the sums of products of coordinates in V and W, with M being capable of being written in the form $$M = \begin{pmatrix} S_{xx} & S_{xy} & S_{xz} \\ S_{yx} & S_{yy} & S_{yz} \\ S_{zx} & S_{zy} & S_{zz} \end{pmatrix}$$

where $$S_{xx} = \sum_{i=1}^{N} x_{v,i} x_{w,i},$$

$$S_{xy} = \sum_{i=1}^{N} x_{v,i} y_{w,i},$$

and so on, and where $\vec{v}_i = [X_{v,i} \ Y_{v,i} \ Z_{v,i}]^t$ and $\vec{w}_i = [X_{w,i} \ Y_{w,i} \ Z_{w,i}]^t$; and compute an optimal translation vector $$\vec{t} = \vec{\mu}_w - R\vec{\mu}_v.$$

where the unit quaternion of interest is the unit eigenvector corresponding to the most positive eigenvalue of the 4×4 symmetric matrix N, where $$N = \begin{pmatrix} S_{xx} + S_{yy} + S_{zz} & S_{yz} - S_{zy} & S_{zx} - S_{xz} & S_{xy} - S_{yx} \\ S_{yz} - S_{zy} & S_{xx} - S_{yy} - S_{zz} & S_{xy} - S_{yx} & S_{zx} - S_{xz} \\ S_{zx} - S_{xz} & S_{xy} - S_{yx} & -S_{xx} - S_{yy} - S_{zz} & S_{yz} + S_{zy} \\ S_{xy} - S_{yx} & S_{zx} + S_{xz} & S_{yz} + S_{zy} & -S_{xx} - S_{yy} + S_{zz} \end{pmatrix}.$$

\* \* \* \* \*